United States Patent
Lowe et al.

(10) Patent No.: US 10,632,098 B2
(45) Date of Patent: Apr. 28, 2020

(54) THERAPEUTIC AGENTS CONTAINING CANNABIS FLAVONOID DERIVATIVE FOR OCULAR DISORDERS

(71) Applicants: Henry I C Lowe, Kingston (JM); Ngeh J. Toyang, Columbia, MD (US)

(72) Inventors: Henry I C Lowe, Kingston (JM); Ngeh J. Toyang, Columbia, MD (US)

( * ) Notice: Subject to any disclaimer, the term of this patent is extended or adjusted under 35 U.S.C. 154(b) by 0 days.

(21) Appl. No.: 16/286,939

(22) Filed: Feb. 27, 2019

(65) Prior Publication Data

US 2019/0262305 A1 Aug. 29, 2019

Related U.S. Application Data

(62) Division of application No. 15/205,534, filed on Jul. 8, 2016, now Pat. No. 10,278,950.

(60) Provisional application No. 62/190,001, filed on Jul. 8, 2015.

(51) Int. Cl.
*A61K 31/352* (2006.01)
*A61K 36/185* (2006.01)

(52) U.S. Cl.
CPC .......... *A61K 31/352* (2013.01); *A61K 36/185* (2013.01)

(58) Field of Classification Search
CPC ........................ A61K 31/352; A61K 36/185
USPC ....................................... 549/403
See application file for complete search history.

(56) References Cited

U.S. PATENT DOCUMENTS

| | | | | |
|---|---|---|---|---|
| 9,687,469 B2 * | 6/2017 | Lowe | ................... | A61K 31/353 |
| 10,278,950 B2 * | 5/2019 | Lowe | ................... | A61K 31/352 |
| 10,398,674 B2 * | 9/2019 | Lowe | ................... | A61K 31/353 |
| 2016/0145230 A1 * | 5/2016 | Lowe | ................... | A61K 31/353 |
| | | | | 514/456 |
| 2018/0353462 A1 * | 12/2018 | Lowe | ................... | A61K 31/352 |
| 2019/0083452 A1 * | 3/2019 | Lowe | ................... | A61K 31/352 |

FOREIGN PATENT DOCUMENTS

| | | | |
|---|---|---|---|
| CN | 103570695 | * 2/2014 | |
| JP | 09301915 | * 11/1995 | |
| WO | WO-2016178713 A1 | * 11/2016 | ........... A61K 31/352 |

OTHER PUBLICATIONS

Dong; Bioorganic & Medicinal Chemistry 2008, 16, 8151-8160. (Year: 2008).*
Jung; Journal of Pharmacy and Pharmacology 2008, 60, 1227-1236. (Year: 2008).*
Minassi; Org. Lett. 2008, 10, 2267-2270. (Year: 2008).*
Yu; Int J Ophthalmol. 2011, 4, 658-669. (Year: 2011).*
Liu; J Clin Lab Anal, 2009, 23, 362-367. (Year: 2009).*
Holder; Bioorganic & Medicinal Chemistry 15 (2007) 6463-6473. (Year: 2007).*
Wordinger; Molecular Vision 2002, 8, 241-250. (Year: 2002).*
Brunelli; Fitoterapia 2009, 80, 327-332. (Year: 2009).*

* cited by examiner

*Primary Examiner* — Daniel R Carcanague

(74) *Attorney, Agent, or Firm* — Royal W. Craig; Gordon Feinblatt LLC

(57) ABSTRACT

The present invention provides a cannabis-based flavonoid pharmaceutical composition including any one or more selected from the group of Apigenin, Cannflavin A, Cannflavin B, Cannflavin C, Chiysoeriol, Cosmosiin and Flavocannabiside or their synthases, for the prevention and treatment of certain ocular diseases and related disorders.

8 Claims, 3 Drawing Sheets

US 10,632,098 B2

THERAPEUTIC AGENTS CONTAINING CANNABIS FLAVONOID DERIVATIVE FOR OCULAR DISORDERS

CROSS-REFERENCE TO RELATED APPLICATIONS

The present application derives priority from U.S. Provisional Patent Application No. 62/190,001 filed 8 Jul. 2015.

BACKGROUND OF THE INVENTION

1. Field of the Invention

The present invention relates to flavonoid derivatives and, more particularly, to cannabis flavonoid derivatives or the pharmaceutically acceptable salt thereof that may be used in a pharmaceutical composition for preventing and treating ocular disorders particularly glaucoma and myopia.

2. Description of the Background

Myopia or Nearsightedness, is the most common refractive error of the eye, and it has become more prevalent in recent years. About 1.6 billion people in the world suffered from myopia in 2000 and the number is expected to rise to 2.5 billion by 2020 (Francisco B M, Salvador M, Amparo N, 2015. Oxidative Stress in Myopia. Oxidative Medicine and Cellular Longevity. Vol 2015 ID: 750637). A study by the National Eye Institute (NEI) shows the prevalence of myopia grew from 25 percent of the U.S. population (ages 12 to 54) in 1971-1972 to a whopping 41.6 percent in 1999-2004. Though the exact cause for this increase in nearsightedness among Americans is unknown, many eye doctors feel it has something to do with eye fatigue from computer use and other extended near vision tasks, coupled with a genetic predisposition for myopia.

Normal and high myopia remains a major medical problem and lead to several eye pathologies such as retinal detachment, glaucoma, macular hemorrhage, cataracts and as such causes visual deterioration and eventually blindness. In an attempt to determine the genetic basis of myopia, studies have shown that a genetic variant of the BIKE (BMP2K) kinase contributes to high myopia (Liu, H. P., Lin, Y. J., Lin, W. Y., Wan, L., Sheu, J. J. C., Lin, H. J., & Tsai, F. J. (2009)). A novel genetic variant of BMP2K contributes to high myopia. *Journal of clinical laboratory analysis*, 23(6), 362-367), Li, Zhi-Kui. "Epidemiology, genetics and treatments for myopia. Int Journal of Ophthamology 2011, 4(6), This genetic variant has as such been identified as a potential therapeutic target for the prevention and correction of myopia.

Flavonoids are common constituents of plants and cover a wide range of functions including acting as yellow pigments in petals and leaves to attract pollinating insects. They might also appear as bluish pigments (anthocyanins) to receive certain wavelengths of light, which permits the plant to be aware of the photoperiod. Many of these flavonoids also protect the plants by being involved in the filtering of harmful ultraviolet light. Some flavonoids play crucial roles in establishing symbiotic fungi, while at the same time they fight infections caused by pathogenic fungi.

Flavonoids have relevant pharmacological activities such as; antioxidant, antidiabetic, anti-inflammatory, antiallergic, antibiotic, antidiarrheal, CNS and against cancer. In particular administration of anthocyanoside oligomer appeared to improve subjective symptoms and objective contrast sensitivity in myopia subjects (Lee, J., Lee, H. K., Kim, C. Y., Hong, Y. J., Choe, C. M., You, T. W., & Seong, G. J. (2005). Purified high-dose anthocyanoside oligomer administration improves nocturnal vision and clinical symptoms in myopia subjects. *British journal of nutrition*, 93(06), 895-899).

Cannabis is credited to have several beneficial pharmacological properties. Unfortunately much attention on Cannabis is focused on its recreational use as a psychoactive drug. Studies have identified over twenty flavonoids in the Cannabis plant, such as; cannflavin A, cannflavin B, cannflavin C, chrysoeril, cosmosiin, flavocannabiside, vitexin, isovitexin, apigenin, kaempferol, myricetin, quercetin, luteolin, homoorientin and orientin (Turner, C. E., Elsohly, M. A., & Boeren, E. G., "Constituents of *Cannabis sativa* L. XVII., A review of the natural constituents", *Journal of Natural Products*, 43(2), 169-234 (1980). The distribution of these flavonoids in the plant varies depending on the type of flavonoid. The total content of flavonoids in the Cannabis' leaves and flowers can reach 1-2.5% of its dry weight depending on environment factors and the variety of the plant.

Cannabis flavonoids have been shown to have several pharmacological properties. Apart from the specific pharmacologic properties identified, cannabis flavonoids are thought to play synergistic roles with other metabolites in the plant. For example, some flavonoids are volatile, lipophilic, permeate membranes, and seem to retain pharmacological properties in cannabis smoke (Sauer, M. A., Rifka, S. M., Hawks, R. L., Cutler, G. B., & Loriaux, D. L., "*Journal of Pharmacology and Experimental Therapeutics*", 224(2), 404-407 (1983). Flavonoids may modulate the pharmacokinetics of THC, via a mechanism shared by CBD, the inhibition of P450 3A11 and P450 3A4 enzymes. These two related enzymes metabolize environmental toxins from pro-carcinogens to their activated forms. P450-suppressing compounds as such serve as chemoprotective agents, shielding healthy cells from the activation of benzo[α]pyrene and aflatoxin B1 (Offord, E. A., Mace, K., Avanti, O., & Pfeifer, A. M., "Mechanisms Involved In The Chemoprotective Effects Of Rosemary Extract Studied In Human Liver And Bronchial Cells", *Cancer Letters*, 114(1), 275-281, (1997), which are two procarcinogenic agents found in cannabis smoke (McPartland, J. M., & Pruitt, P. L., "*Alternative Therapies In Health And Medicine*", 5(4), 57 (1999). Cannabis flavonoids thus may be modulating the therapeutic effects of THC and CBDs by either synergistically enhancing desired pharmacologic effects or reducing detrimental effects.

Given the abundance of evidence supporting the health benefits of cannabis flavonoids, the present inventors have successfully synthesized rare cannabis flavonoids including cannflavin A, cannflavin B and cannflavin C, isocannflavin B and their analogs have demonstrated ability to inhibit the BMP2K kinase which has implication in the development of myopia. The present invention relates to the use of the newly synthesized flavonoids alone or in combination with other flavonoids or related bioactive compounds particularly the cannabinoids to treat or prevent ocular diseases shown to be inhibited by the use of these flavonoids and the drug combinations.

SUMMARY OF THE INVENTION

It is, therefore, an object of the invention to provide a pharmaceutical composition for the prevention and treatment of ocular diseases using specific cannabis-based flavonoid compounds.

It is another object to provide a method for isolating specific cannabis-based flavonoid pharmaceutical compositions from raw plant material that are biologically active in the prevention and treatment of ocular disease.

It is still another object to provide a method for synthesizing said specific cannabis-based flavonoid pharmaceutical compositions.

In accordance with the foregoing objects, the present invention provides a flavonoid-based pharmaceutical composition for the prevention and treatment of ocular disease having the structure of the general formula of FIG. 1 or a pharmaceutically acceptable salt thereof.

The present invention is a group of cannabis-based flavonoid pharmaceutical compositions selected from among the group of Apigenin, Cannflavin A, Cannflavin B, Cannflavin C, Chrysoeriol, Cosmosiin and Flavocannabiside useful for the prevention and treatment of certain ocular diseases.

The cannabis-based flavonoid pharmaceutical composition for the prevention and treatment of diseases has the structure of the general formula of FIG. 1 or a pharmaceutically acceptable salt thereof.

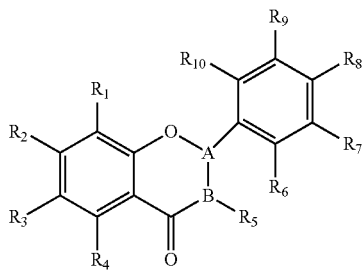

Figure 1

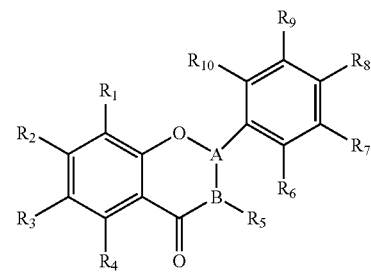

Figure 1

Wherein,

R1-R10 may be any one or more substituents selected from the group consisting of a hydrogen molecule (H), a hydroxide molecule (OH), a methyl group comprising one carbon atom bonded to three hydrogen atoms (CH3), an alkoxy group (O—CH3), a carboxyl group (COOH), chlorine (Cl), Bromine (Br), Fluorine (F), Glutamic acid (Glu), geranyl chain, prenyl chain and any salts or derivatives of the foregoing. A and B may each be either a single or double bond.

A method for the prevention and treatment of ocular disease is also disclosed using the specific cannabis-based flavonoid pharmaceutical compositions above is also disclosed, as well as a method for isolating the specific flavonoid-based pharmaceutical compositions from raw plant material, and a method for synthesizing said flavonoid-based pharmaceutical compositions.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Reference will now be made in detail to preferred embodiment of the present invention, examples of which are illustrated in the accompanying drawing.

Wherein,

R1-R10 may be any one or more substituents selected from the group consisting of a hydrogen molecule (H), a hydroxide molecule (OH), a methyl group comprising one carbon atom bonded to three hydrogen atoms (CH3), an alkoxy group (O—CH3), a carboxyl group (COOH), chlorine (Cl), Bromine (Br), Fluorine (F), Glutamic acid (Glu), a geranyl chain or prenyl chain and any salts or derivatives of the foregoing. A and B may each be either a single or double bond.

Figure 2:
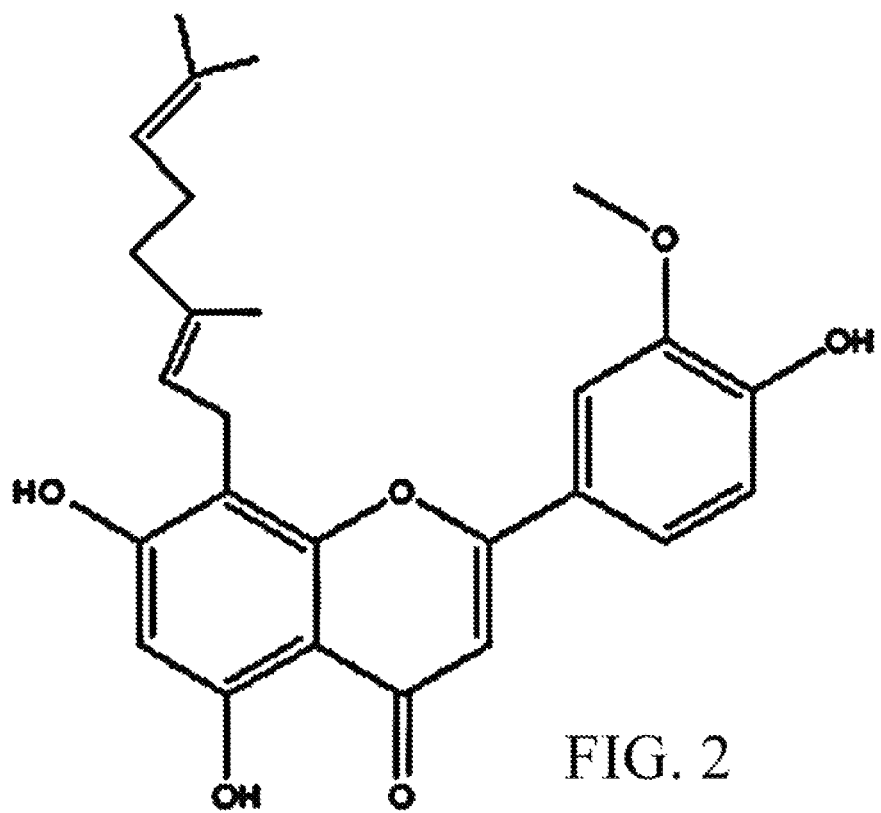
FIG. 2 is the structure of the specific cannabis-based flavonoid pharmaceutical composition.

The most preferred structure of the synthesized flavonoid presented in FIG. 2.

Figure 1:
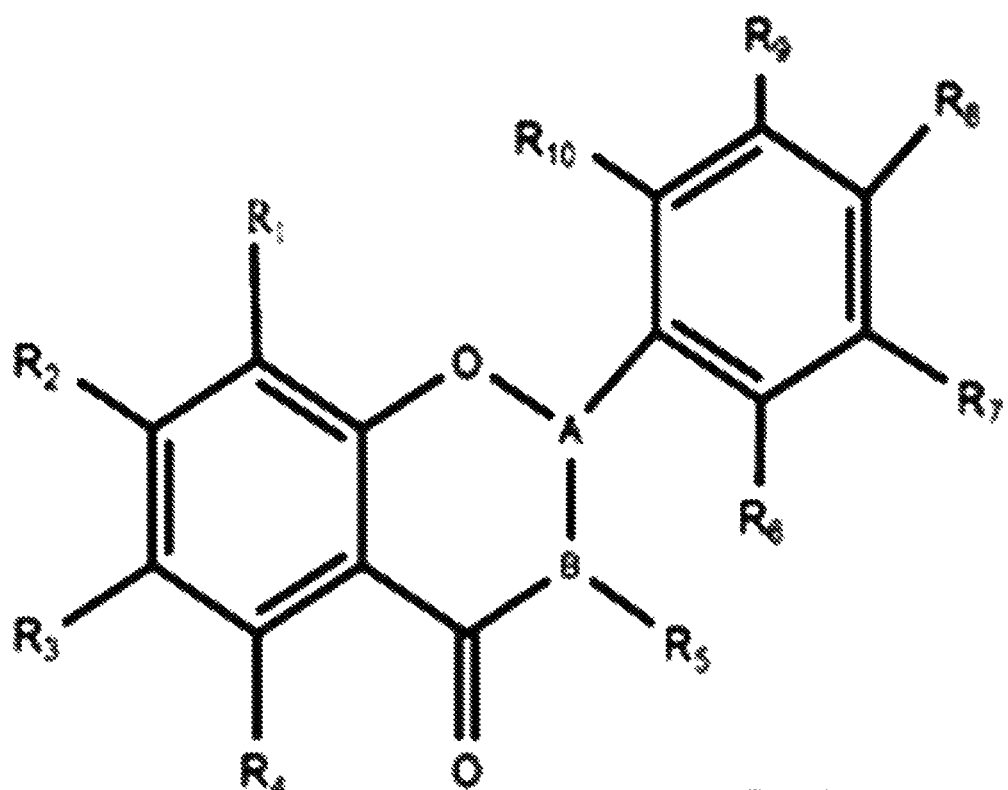
FIG. 1 is an illustration of the general cannabis-based flavonoid pharmaceutical compositions according to the present invention.

In an embodiment, a method for the prevention and treatment of ocular disorders using the specific cannabis-based flavonoid pharmaceutical compositions above is also disclosed. Administration may be by various routes including oral, rectal or intravenous, epidural muscle, subcutaneous, intrauterine, or blood vessels in the brain (intracerebroventricular) injections. The flavonoid derivatives of the general and specific formulas (FIGS. 1-2) according to the present invention and a pharmaceutically acceptable salt thereof may be administered in an effective dose, depending on the patient's condition and body weight, extent of disease, drug form, route of administration, and duration, within a range of from 0.1 to 500 mg between 1-6 times a day. Of course, most dosages will be by a carrier. The specific dose level and carrier for patients can be changed according to the patient's weight, age, gender, health status, diet, time of administration, method of administration, rate of excretion, and the severity of disease.

The composition may be formulated for external topical application, oral dosage such as powders, granules, tablets, capsules, suspensions, emulsions, syrups, aerosols, suppositories, or in the form of a sterile injectable solution. Acceptable carriers and excipients may comprise lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Bioactivity of the above-described compounds has been verified by use of kinase inhibition assays to determine the effect of the cannabis flavonoids in the onset and progression of ocular disorders. The inhibition of BIKE (BMP2K) kinases in particular has been shown to be a therapeutic target that could block the onset and progression of ocular disorders.

Kinase Inhibition Assay

Cannabis flavonoids and their analogs were subjected to kinase inhibition assay. The compounds were first screened at a single concentration of 10 μM in the primary assay. Compounds inhibiting at least 70% of specific kinases were subjected to further screening to determine kd values. To determine the kd values, competition binding assays were established, authenticated and executed as described previously (Fabian et al., 2005, Karaman et al., 2008). For most assays, kinases were fused to T7 phage strains (Fabian et al. 2005) and for the other assays, kinases were produced in HEK-293 cells after which they were tagged with DNA for quantitative PCR detection (data not shown). In general, full-length constructs were used for small, single domain kinases, and catalytic domain constructs for large multi-domain kinases. The binding assays utilized streptavidin-coated magnetic beads treated with biotinylated small molecule ligands for 30 minutes at room temperature which generated affinity resins for the kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and diluted directly into the assay (Final DMSO concentration=2.5%). All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by quantitative PCR. Kd values were determined using a standard dose response curve using the hill equation. Curves were fitted using a non-linear least square fit with the Levenberg-Marquardt algorithm.

A method for isolating the specific cannabis-based flavonoid pharmaceutical compositions from raw plant material is also disclosed. The Cannabis flavonoid and derivatives were isolated and synthesized as described in PCT application PCT/US15/62331.

Figure 3:
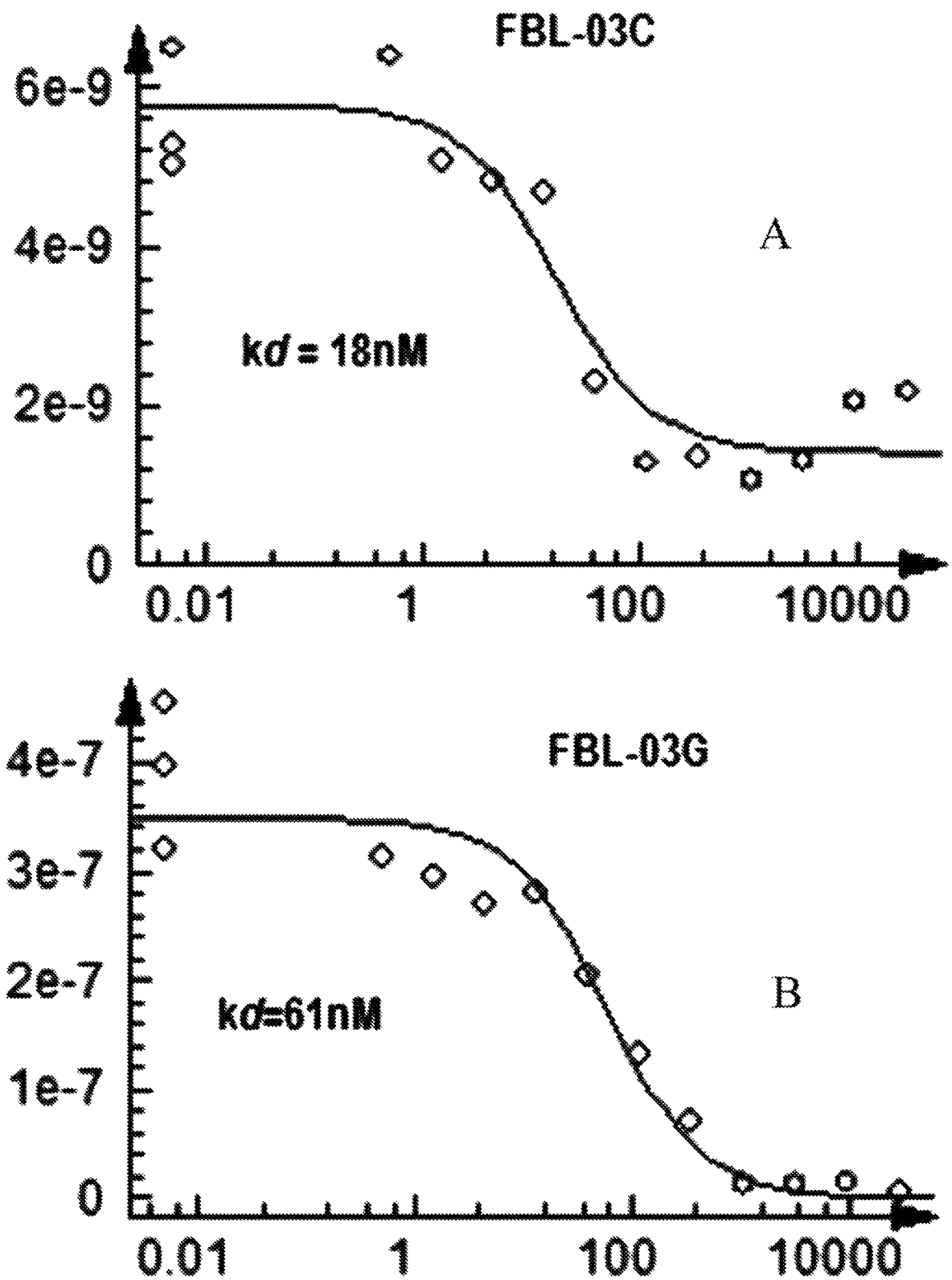
FIG. 3 is the dose response curve for the inhibition of BIKE (BMP2K) kinase by cannabis flavonoid derivatives
Figure 4:
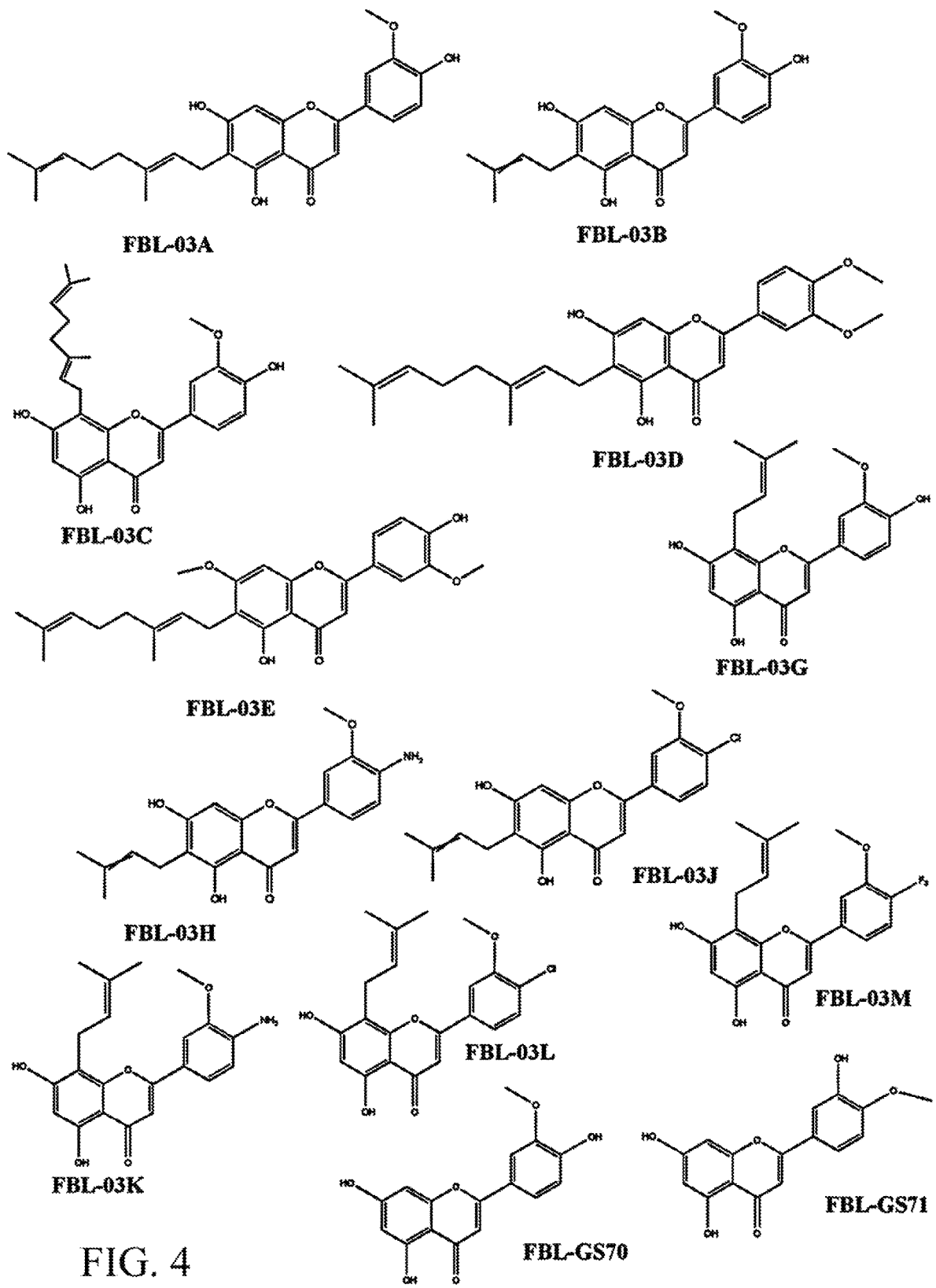
FIG. 4 is the structures of related cannabis flavonoid derivatives.

FIG. 3 is the dose response curve for the inhibition of BIKE (BMP2K) kinase by cannabis flavonoid derivatives FIG. 4 illustrates the structure of closely related cannabis flavonoid derivatives considered to be within the scope and spirit of the invention.

It should now be apparent that the above-described invention provides a pharmaceutical composition for the prevention and treatment of disease with specific cannabis-based flavonoid derivatives a method for the prevention and treatment of disease using the specific cannabis-based flavonoid pharmaceutical compositions.

It is to be understood, therefore, that the invention may be practiced otherwise than as specifically set forth in the appended claims.

The invention claimed is:

1. A method for treatment of glaucoma or myopia, comprising:
    administering to a patient in need thereof, a compound having a chemical structure as shown below, or any pharmaceutically acceptable salt thereof:

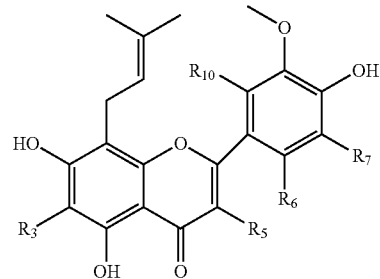

wherein, $R_3$, $R_5$, $R_6$, $R_7$, and $R_{10}$ are independently selected from the group consisting of: a hydrogen, a hydroxyl group, a methyl group, an alkoxy group, a carboxyl group, chlorine, bromine, fluorine, glutamic acid, a geranyl chain, and a prenyl chain.

2. The method of claim 1, wherein the administration to the patient of the compound comprises administering the compound via a route selected from the group consisting of: a topical route, an oral route, and a rectal route.

3. The method of claim 1, wherein the administration to the patient of the compound comprises injecting the compound into a location of the patient's body selected from the group consisting of: a vein, an epidural muscle, a subcutaneous location, an intrauterine location, and an intracerebroventricular location.

4. The method of claim 1, further comprising:
    selecting a dose of the compound based on at least one factor selected from the group consisting of: the patient's condition, the patient's body weight, an extent of the ocular disorder, a form of the compound, a route of administration of the compound, and a duration of administration;
        wherein the administration to the patient of the compound comprises administering the selected dose of the compound.

5. The method of claim 1, further comprising:
    selecting a dose of the compound;
        wherein the administration to the patient of the compound comprises administering between 1 to 6 of the selected doses of the compound each day.

6. The method of claim 1, further comprising:
    selecting a dose of the compound within a range from 0.1 milligrams (mg) to 500 mg;
        wherein the administration to the patient of the compound comprises administering the selected dose of the compound.

7. The method of claim 1, wherein the administration of the compound comprises administering a composition comprising the compound and a carrier substance selected from the group consisting of: lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

8. The method of claim 1, wherein the administration of the compound comprises administering a composition formulated in a form selected from the group consisting of: a powder, a granule, a tablet, a capsule, a suspension, an emulsion, a syrup, an aerosol, a suppository, and an injectable solution.

* * * * *